United States Patent [19]

Rayburn et al.

[11] Patent Number: 5,733,242
[45] Date of Patent: Mar. 31, 1998

[54] INTUBATION SYSTEM HAVING AN AXIALLY MOVEABLE MEMORY CYLINDER

[76] Inventors: Robert L. Rayburn, 669 12th Ave., Salt Lake City, Utah 84103; Scott D. Unice, 1465 Sherman Ave., Salt Lake City, Utah 84105

[21] Appl. No.: 598,113

[22] Filed: Feb. 7, 1996

[51] Int. Cl.$^6$ .................................................. A61B 1/012
[52] U.S. Cl. ........................ 600/120; 600/136; 600/143
[58] Field of Search .................................... 600/114, 120, 600/125, 185, 188, 194, 136, 143

[56] References Cited

U.S. PATENT DOCUMENTS

| | | |
|---|---|---|
| 1,704,764 | 3/1929 | Schellberg . |
| 3,677,262 | 7/1972 | Zukowski ............................ 600/120 |
| 3,776,222 | 12/1973 | Smiddy . |
| 4,254,762 | 3/1981 | Yoon ................................... 600/114 |
| 4,444,185 | 4/1984 | Shugar . |
| 4,567,882 | 2/1986 | Heller . |
| 4,577,621 | 3/1986 | Patel .................................. 600/114 |
| 4,580,556 | 4/1986 | Kondur ............................ 600/120 X |
| 4,624,243 | 11/1986 | Lowery et al. ................... 600/114 X |
| 4,659,195 | 4/1987 | D'Amelio .......................... 600/114 X |
| 4,784,117 | 11/1988 | Miyazaki .......................... 600/114 X |
| 5,005,559 | 4/1991 | Blarco et al. ....................... 600/114 |
| 5,131,380 | 7/1992 | Heller . |
| 5,163,941 | 11/1992 | Garth et al. . |
| 5,183,031 | 2/1993 | Rossaff . |
| 5,327,881 | 7/1994 | Greene ................................ 600/120 |
| 5,551,946 | 9/1996 | Bullard ........................... 600/114 X |

FOREIGN PATENT DOCUMENTS 719538  12/1954  United Kingdom ................... 600/114

OTHER PUBLICATIONS

Rayburn, Light Wand Intubation, 1978.
Brochure, Olympus Tracheal Intubation Fiberscope LF2.
Management at the Difficult Adult Airway, Benumof, Anethemology V75; No. 6 pp. 1087–1110, 1991.

*Primary Examiner*—Richard J. Apley
*Assistant Examiner*—John P. Leubecker
*Attorney, Agent, or Firm*—Roylance, Abrams, Berdo & Goodman, L.L.P.

[57] ABSTRACT

An intubator includes a housing and a memory cylinder connected for axial movement relative to the housing. A flexible scope tube attached to the housing extends within and through the memory cylinder such that the scope tube can be retracted within or caused to extend beyond the distal end of the memory cylinder by the relative axial movement between the housing and memory cylinder. The scope tube is angularly adjustable and includes a light transmitting fiber optic cable, a visual transmission fiberoptic cable, and a fluid conduit. In use, an endotracheal tube is mounted on the memory cylinder such that the endotracheal tube, memory cylinder and scope tube have their distal ends flush. The intubator is then inserted through the patient's mouth to the larynx opening. Collapsing the memory cylinder within the handle causes the scope tube to be extended from the memory cylinder for positioning within the trachea. The endotracheal tube can then be located within the trachea using the scope tube as a stylet or guide.

23 Claims, 4 Drawing Sheets

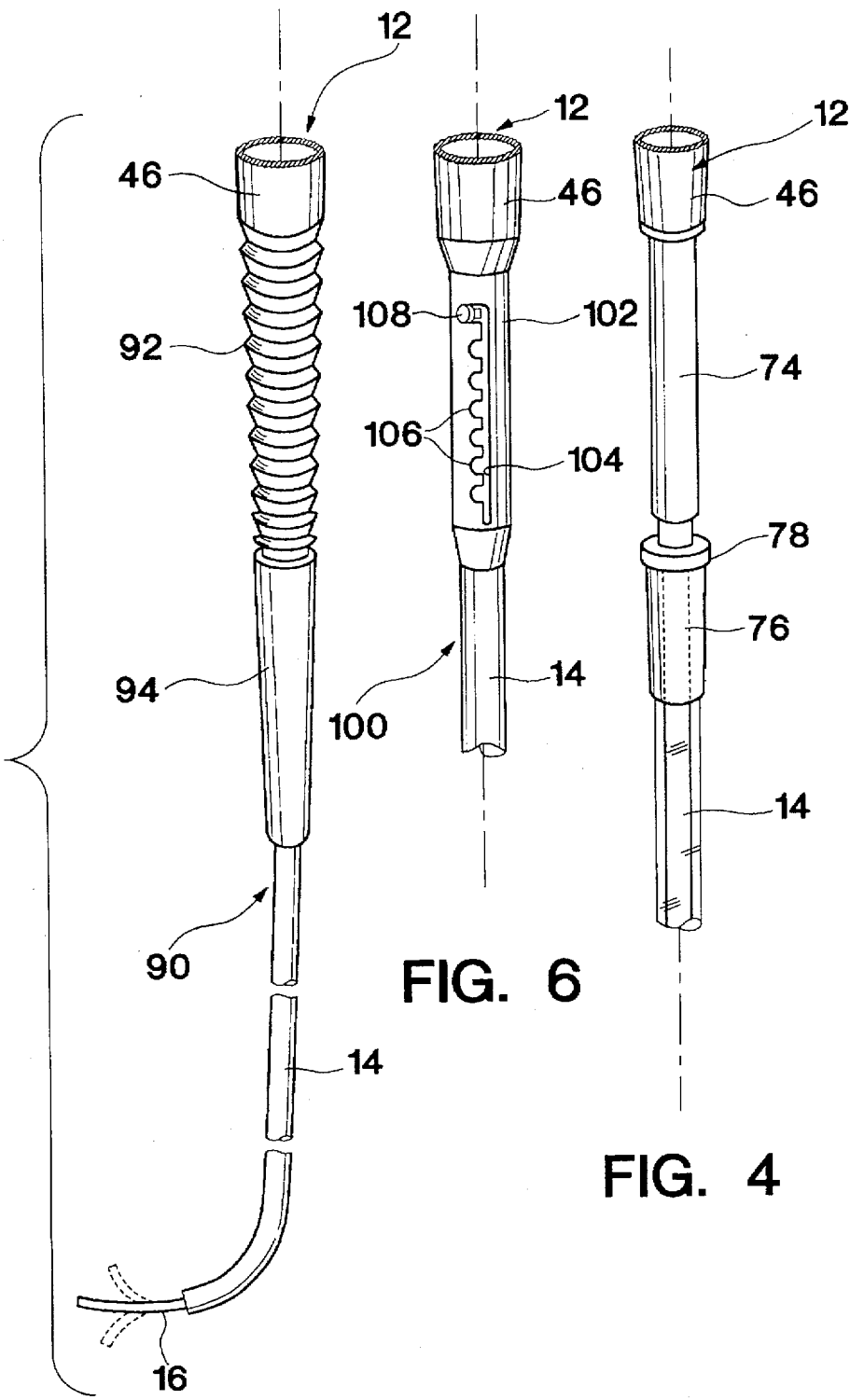

INTUBATION SYSTEM HAVING AN AXIALLY MOVEABLE MEMORY CYLINDER

FIELD OF THE INVENTION

The present invention relates to a system for inserting an endotracheal tube within a patient. More particularly the present invention relates to a fiberoptic intubator system having an axially adjustable memory cylinder and an angularly adjustable scope tube, with light and visual fiberoptic cables and with a fluid conduit, which is slidably received in the memory cylinder to permit relative axial movement of the scope tube relative to the memory cylinder.

BACKGROUND OF THE INVENTION

Current endotracheal intubation is effected in the majority of cases by use of a rigid laryngoscope inserted through the mouth. The laryngoscope uses a straight or curved blade with a light. By direct visualization, an endotracheal tube is placed through the vocal cords into the trachea.

In cases where direct visualization of the opening to the larynx is not possible, difficulties, injury, or failure of intubation may occur. This inability to visualize the glottic opening may occur in patients for many reasons, including short muscular neck, prominent teeth, receding lower jaw (Pierre Robin Syndrome), inability to open the mouth sufficiently (arthritis), inability to position the head properly (cervical spine injuries), masses in the oropharynx or larynx, or other anatomic anomalies.

If a difficult intubation for one of the foregoing reasons is anticipated in advance (elective or non-emergent situation), certain methods and devices would then be used to secure the airway. Initially, the patient is given oxygen by face mask if the patient is spontaneously breathing or by positive pressure ventilation if the patient is unconscious or anesthetized. Devices, such as nasal pharyngeal airways, oropharyngeal airways, laryngeal masks, or esophageal airways may be inserted blindly (without the aid of a laryngoscope) to assist delivery of oxygen to the patient. However, none of these devices enter the trachea. Therefore, such devices do not provide a permanent solution for intubation of the trachea which is necessary for the prevention of aspiration, ventilator therapy or certain surgical procedures.

In the non-emergent situation, frequently intubation is accomplished over a flexible fiberoptic bronchoscope or fiberoptic laryngoscope. These devices are expensive and very delicate, and require considerable expertise to use effectively. In the non-emergent case, frequently an expert with this equipment will be notified in advance, since neither are usually readily available on short notice. These devices usually require two operators, one to provide oxygen to the patient, and the second, using both hands, to operate the flexible scope. Also the construction and flexibility of these devices makes them awkward, even in the expert's hands, especially for orotracheal intubation.

The intubation procedure may take many minutes or longer due to the clearing of secretions and focusing necessary to find the orifice of the larynx, and then to manipulate the device further into the trachea. Any movement of the oropharynx from breathing or swallowing will dislodge these flexible devices causing loss of visualization.

In an emergency situation where the above methods to temporarily assist in the delivery of oxygen are unsuccessful, or only partially successful, intubation of the trachea must be accomplished immediately. The flexible fiberoptic laryngoscope or bronchoscope is generally not sufficiently adequate as a quick solution for the reasons previously mentioned. Previously known devices for the difficult and emergent intubation include fiberoptic intubating laryngoscope, such as the Bullard scope and the Upshere laryngoscope. These devices allow better visualization of the larynx in some cases. However, their blades are preformed and placement of an endotracheal tube through or around such devices does not direct the endotracheal tube into the larynx. Also, the problem of quickly finding the orifice of the larynx exists, as with the flexible fiberoptic laryngoscope and bronchoscope due to movement and secretions, although due to their sturdy construction, once in place visualization should be maintained. None of these fiberoptic intubating scopes have models small enough to be used in the smallest of children, and are, therefore, not helpful in difficult airways of small children and infants.

U.S. Pat. No. 4,444,185 to Rossoff discloses a type of flexible fiberoptic bronchoscope or flexible fiberoptic laryngoscope, except that it is rigid for shaping of the shaft with a flexible tip. The rigidity of the shaft allows more control, but the flexible tip is still affected by movement in the oropharynx and makes finding the larynx slow and cumbersome. The preformed curve to the shaft makes advancement of any appreciable length of the scope into the trachea cumbersome. This lack of sufficient length into the trachea allows for the possibility of the endotracheal tube "popping" out of the trachea upon withdrawal of the scope.

If one is not able by these methods to intubate the trachea to deliver oxygen, then the trachea must be entered transcutaneously (through the outside of the neck). This means a cricothyroidotomy, tracheostomy, or transtracheal jet ventilation must be performed. These methods performed even in experienced hands may be unsuccessful or cause complications such a pneumomediastinum, pneumothorax, bleeding, vocal cord paralysis, thyroid injury, etc.

SUMMARY OF THE INVENTION

An object of the present invention is to provide an apparatus for and a method of intubating a patient which can be easily and quickly used in a wide variety of emergency and non-emergency situations.

Another object of the present invention is to provide an apparatus for and a method of intubating a patient which can be simply adapted for young or small patients.

A further object of the present invention is to provide an apparatus for and a method of intubating a patient where a flexible scope tube can be advanced into the patient's trachea, independently of the remainder of the device for assisting in proper positioning of the endotracheal tube.

The foregoing objects are basically obtained by an intubator comprising a housing having first and second ends, a memory cylinder mounted for axial movement within and relative to the housing and a scope tube coupled to and extending into the housing and slidably received in the memory cylinder. The memory cylinder extends from the second axial end of the housing and has a first axial end section received in the housing and a second axial end section spaced from the second axial end of the housing. The scope tube includes a light transmitting fiberoptic cable, a visual transmission fiberoptic cable and a fluid conduit. Each of the cables and the conduit have a near end in the housing and a distal end remote from the housing. Adjustment means can vary the angular orientation of the cable and conduit distal ends relative to their near ends. The housing additionally includes light means for directing light into the light transmitting fiberoptic cable and emitting light from its distal end, lens means for viewing images adjacent the cable distal ends through the visual transmission fiberoptic cable, and coupling means for connecting fluid means to the near end of the fluid conduit to convey fluids between fluid conduit near and distal ends.

By forming the intubator in this manner, the intubator can be initially positioned using the memory cylinder aided by the direct visualization of its positioning through the fiberoptic cable. Once the memory cylinder is in position, the angularly adjustable and flexible scope tube can be moved axially through the memory cylinder into the trachea to the desired position. Once the scope tube is fully inserted within the trachea, the memory cylinder and the scope tube can be used to guide an endotracheal tube into its fully inserted and proper position within the patient. Once the endotracheal tube is fully positioned, the scope tube can be withdrawn into the memory cylinder and the intubator can be withdrawn from the endotracheal tube to allow proper treatment of the patient. The fluid conduit permits the suctioning of fluids from the patient or the administering of such fluids as local anesthetic and oxygen into the patient during the intubation procedure.

The foregoing objects are also obtained by a method of intubating a patient, comprising the steps of mounting an endotracheal tube on an intubator having a housing, memory cylinder and a scope tube axially slidable in the memory cylinder, with distal ends of the memory cylinder, endotracheal tube and scope tube being flush; illuminating a light source and conducting light through a light fiberoptic cable in the scope tube; bending a distal end of the memory cylinder into a curve of between about 45 degrees and about 90 degrees; inserting the distal end of the memory cylinder into a patient's oral pharynx and behind the patient's tongue; positioning the handle in a vertical plane; manipulating the patient's larynx orifice by a light reflex emitted from the distal end of the scope tube and through the patient; advancing the scope tube from the memory cylinder, by collapsing the intubator at an axially adjustable connection between the housing and the memory cylinder, and into the patient's larynx and trachea, while viewing the larynx and trachea through a visual fiberoptic cable in the scope tube; locking the axially adjustable connection between the housing and the memory cylinder; pushing the endotracheal tube from the memory cylinder and into the patient's trachea using the scope tube as a guide, while visually confirming placement of the endotracheal tube in the trachea through the visual fiberoptic cable; and withdrawing the intubator from the patient, while leaving the endotracheal tube in the patient.

Other objects, advantages and salient features of the present invention will become apparent from the following detailed description, which, taken in conjunction with the annexed drawings, discloses preferred embodiments of the present invention.

BRIEF DESCRIPTION OF THE DRAWINGS

Referring to the drawings which form a part of this disclosure:

FIG. 4 is a partial, side elevational view of the connection between the memory cylinder and the housing of the intubator of FIG. 1;

FIG. 5 is a partial, side elevational view of the connection between the memory cylinder and the housing of an intubator according to a second embodiment of the present invention;

FIG. 6 is a partial, side elevational view of the connection between the housing and the memory cylinder of an intubator according to a third embodiment of the present invention;

DETAILED DESCRIPTION OF THE INVENTION

Figures 1, 2:
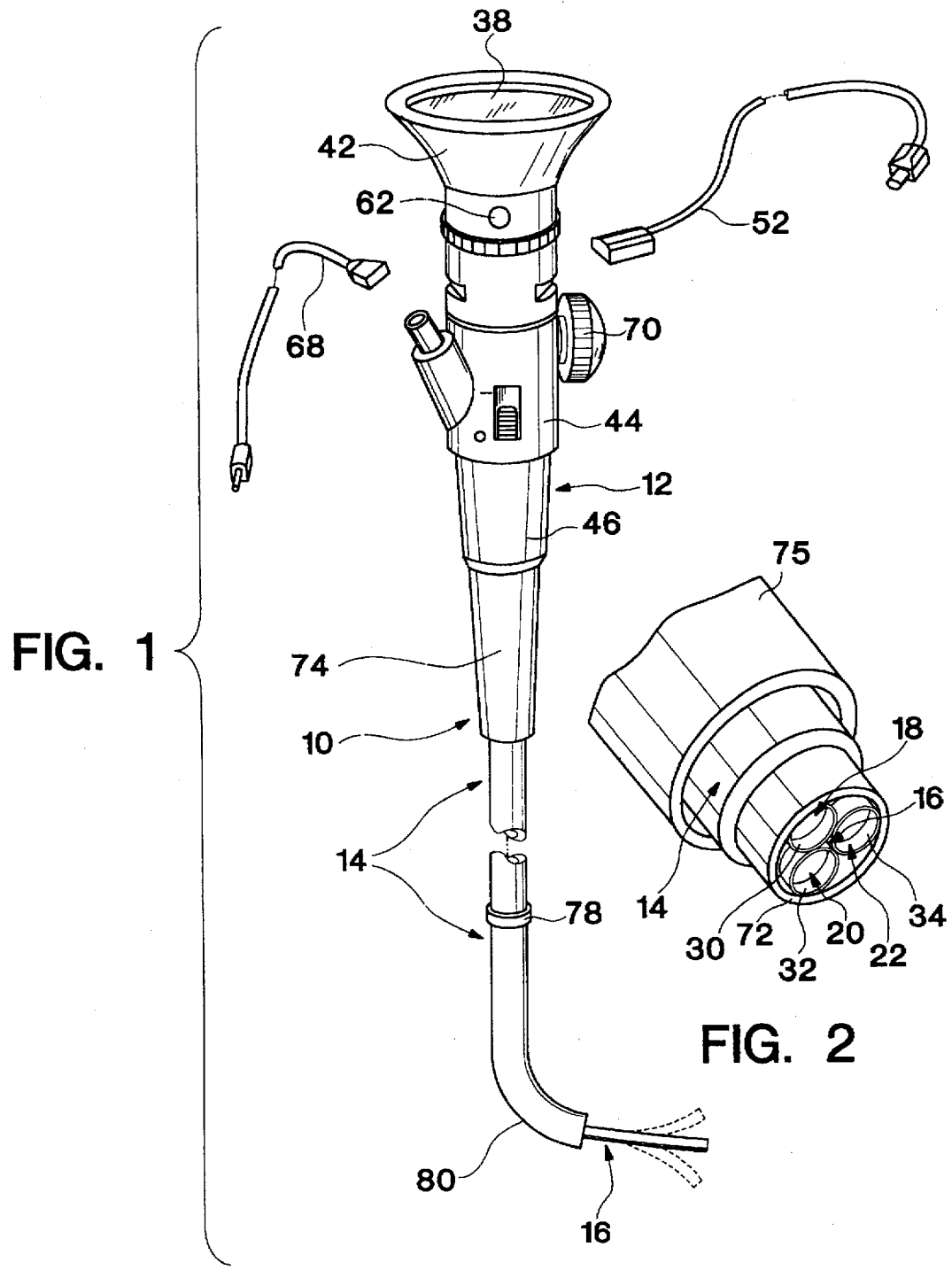
FIG. 1 is a partial, perspective view of an intubator according to a first embodiment of the present invention.
FIG. 2 is an enlarged, partial perspective view of the distal ends of the memory cylinder and the scope tube of FIG. 1.

Referring initially to FIG. 1, an intubator 10 according to a first embodiment of the present invention comprises a housing or handle 12, a memory cylinder 14 mounted for axial movement within and relative to the housing, and a flexible scope tube 16 slidably received within the memory cylinder.

Figure 3:
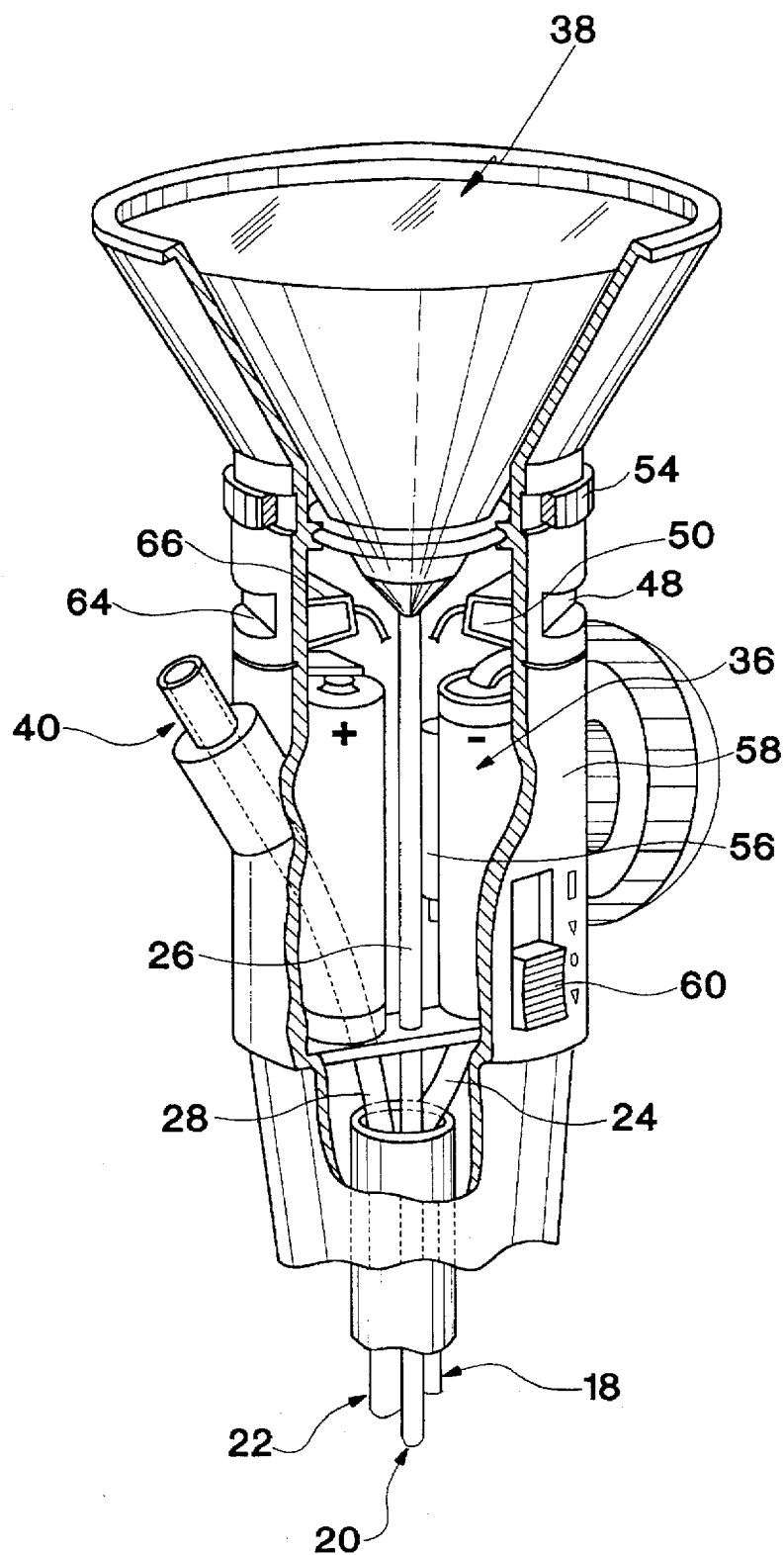
FIG. 3 is an enlarged, perspective view, partially in section, of the housing of the intubator of FIG. 1.

As illustrated in FIGS. 2 and 3, scope tube 16 contains a light transmitting fiberoptic cable 18, a visual transmission fiberoptic cable 20 and a fluid conduit 22. Near ends 24, 26 and 28 of cable 18, cable 20 and conduit 22, respectively, are mounted in housing 12. Distal ends 30, 32 and 34 of cable 18, cable 20 and conduit 22, respectively, are spaced and remote from housing 12.

Housing 12 comprises light source 36 for directing light into the light transmitting fiberoptic cable 18 and emitting light from its distal end 30, a lens 38 for viewing images adjacent distal end 32 through the visual transmission fiberoptic cable 20, and a coupling 40 for connecting a fluid source to near end 28 of fluid conduit 22 for suctioning fluids from the patient at distal end 34 or administering fluids to the patient through the fluid conduit.

Housing 12 comprises a frustoconical top section 42, a substantially right circular cylinder middle section 44 and a tapered bottom section 46. Top section 12 supports lens 38 and tapers toward middle section 44. Bottom section 46 tapers away from middle section 44.

Lens 38 is connected to near end 26 of fiberoptic cable 20 to permit the operator to view the patient through fiberoptic cable 20 at the exposed, upper end of lens 38. The lens can be treated to prevent fogging. An optical port 48 opens on middle section 44, and includes an optical connector 50. Optical connector 50 is suitably coupled to visual cable 20 for attaching an optical cord 52 which can be coupled to a monitor (not shown). In this manner, the operator can view the intubation through the monitor, rather than through lens 38. When viewing through lens 38, a focusing ring 54 is provided in the housing to enable the operator to focus the lens. The focusing ring and its attachment to the lens for adjustment of the lens is conventional, as thus, is not described in detail.

Light source 36 includes a light bulb device 56 and batteries 58. The batteries provide electrical power to the light bulb device coupled to near end 24 of light transmission cable 18. A switch 60 connected to the light bulb device and the batteries controls the operation of the light source. A warning light 62 can be provided on the housing for indicating low battery power and the need to replace the batteries. The batteries can be removed and installed through suitable access door(s) provided in housing middle section 44.

If an additional light source is necessary, housing 12 has a light port 64. Light port 64 includes a light connector 66 for connecting an external light source to light transmission cable 18 through a light cord 68. Light cord 68 is coupled to light connector 66 through light port 64.

Coupling 40 is in the nature of a syringe port which forms an exterior opening for near end 28 of fluid conduit 22. This port can take a variety of different shapes and can be provided in different numbers depending on the need in operating the intubator and the size of the intubator. A fluid means, for example, a syringe, can be connected to coupling 40 for passing medication through the fluid conduit and out distal end 34 for administering the medication to the patient at the location of distal end 34. Alternatively, a suction source can be attached to the port for suctioning fluids from the patient at distal end 34. If oxygen is necessary, an oxygen source can be connected to coupling 40 and administered to the patient through fluid conduit distal end 34.

An adjustment knob 70 is mounted on housing middle section 44. As is conventional with fiberoptic scopes in the medical field, knob 70 is connected through an adjustment cable 72 to the distal end of scope tube 16. Turning knob 70 varies the angular orientation of the scope tube distal end relative to its near end. Such angular adjustment is graphically depicted by the phantom lines in FIG. 1. The outer diameter of the scope tube can be approximately 1.2 mm.

A rigid tube tubular connector 74 extends coaxially from the lower end of housing bottom section 46. The cross sectional configuration of tube 74 can be circular, but can also be any other suitable shape. This tube provides the axially adjustable connection of memory cylinder 14 to housing 12 in the first embodiment of the present invention. Tube 74, which forms a part of housing 12, telescopically and frictionally engages the upper axial end section of the memory cylinder.

Memory cylinder 14 is formed of a semi-rigid metal enabling the memory cylinder to flex or bend without binding or forming a kink extending into its interior which would prevent relative axial movement of the scope tube though the memory cylinder, and without forming a pinch or otherwise damaging the scope tube. Alternatively, the memory cylinder can be made of a suitable plastic. The exterior surface of the memory cylinder can be coated with an anti-friction coating, e.g., teflon or other material, to facilitate the mounting and disengagement of an endotracheal tube 75 (FIG. 2). The length of the memory cylinder is chosen such that it extends for a distance of approximately 40–48 cm from the end of the handle to the blunt tip of the intubator (i.e., distal end of the memory cylinder). The outside diameter can vary from 3.0 mm to approximately 8.5 mm in various models of the intubator, depending on whether the intubator is to be used in a pediatric environment or an adult environment. Alternatively, the memory cylinder can taper from the outside diameter of 8.5 mm adjacent the handle to an outside diameter of 3.0 mm at its distal end. The outside surface of a tapered memory cylinder would not be coated with an antifriction coating, but would have a friction fitting surface for holding an outer or proximal end of an endotracheal tube (as shown, for example, by friction fitting 94 in FIG. 5).

A securing ring 78 is attached to the outside surface of memory cylinder 14 intermediate its axial end sections. The ring is movable, but with considerable resistance, along the length of the memory cylinder to the point where memory cylinder 14 is received within tube 74. The outer lateral surface of the securing ring is modestly tapered toward the distal end of the memory cylinder. The proximal or near female end of endotracheal tube 75, after being mounted over the memory cylinder, can be forced onto securing ring 78 and then moved with the securing device so that the distal end of the endotracheal tube is adjacent or flush with the distal end of the memory cylinder.

The securing ring can vary in diameter from the small diameter distal end portion of the memory cylinder to the relatively larger near or upper axial end section of the memory cylinder. Alternatively, the securing ring or device can be attached to the outside or the proximal end of the endotracheal tube by a capping or tooth device that may vary in diameter by a sliding device. Such devices are commonly used and the industry and are conventional such that they are not described further in detail.

Memory cylinder 14 can also be detachable from housing tube 74. A snap connection fitting can be provided between housing tube 74 and the memory cylinder to enable different memory cylinders to be engaged with or attached to housing 12. In this manner, memory cylinders of different widths and lengths can be quickly and easily attached to housing 12.

Distal end section 80 of memory cylinder 14 is curved or bent at an angle relative to the remainder thereof. The degree of curving or bending can be adjusted manually or mechanically in a goose-neck type of adjustment. A curve of approximately 90 degrees in the memory cylinder distal axial end section facilitates curving of the memory cylinder around the back of the tongue into the orifices of the patient's larynx.

Within memory cylinder distal end section 80 in the orifice of the patient's larynx, scope tube 16 can be extended from the memory cylinder and adjusted, using knob 70 to "snake" the scope tube into the patient's trachea. The scope tube is extended from the memory cylinder by axially telescoping memory cylinder 14 within housing tube 74. This telescoping action moves the distal end of the scope tube out of the memory cylinder. The distal end of the memory cylinder is made to be blunt to facilitate insertion and prevent tissue injury.

FIG. 4 illustrates the intubator according to the first embodiment of the present invention, with a movable securing ring 78 having a tapered lower part 76 to which a standard endotracheal tube can be attached. The tapering facilitates connection of endotracheal tubes of different sizes. The telescoping arrangement of housing tube 74 and memory cylinder 14 is represented. When the memory cylinder is withdrawn into housing tube 74, scope tube 16 is deployed from the memory cylinder distal axial end section. When the memory cylinder is telescoped out of housing tube 74, the scope tube is retracted within the memory cylinder and the endotracheal tube is moved away from the housing.

FIG. 5 illustrates an intubator 90 according to a second embodiment of the present invention which varies from the first embodiment in two ways. First, the connection of memory cylinder 14 to housing 12, in this embodiment, comprises a tubular connector in the form of a collapsible bellows 92. Second, below the bellows, a relatively long, non-movable, tapered friction fitting 94 is provided for securing the proximal ends of variously sized endotracheal tubes (without their 15 mm adapters) about the memory cylinder. Collapsing or extending bellows 92 moves scope 16 and housing 12 relative to memory cylinder 14. Securing ring 78 and friction fitting 94 can be used interchangeably on the different embodiments.

FIG. 6 illustrates an intubator 100 having a housing 12 with a tubular connector 102 extending from the housing which slidably receives and connects the memory cylinder to the housing for relative axial adjustment or sliding action. Tubular connector 102 includes a rachet mechanism for controlling the relative axial movement between memory cylinder 14 and housing tubular connector 102. The rachet mechanism comprises a slot 104 which extends axially along the tubular connector. The slot has a series of steps 106 spaced along the axial length of the tubular connector. A laterally projecting cog 108 on the upper or near axial end section of memory cylinder 14 is slidably received in the slot and can be releasably and selectively engaged with the respective steps. By moving the cog, which is fixed to the memory cylinder, the memory cylinder is moved axially relatively to the tubular connector. The relative axial positions of the tubular connector and the memory cylinder are then releasably set by locating the cog in one of the steps 106.

Figure 7:
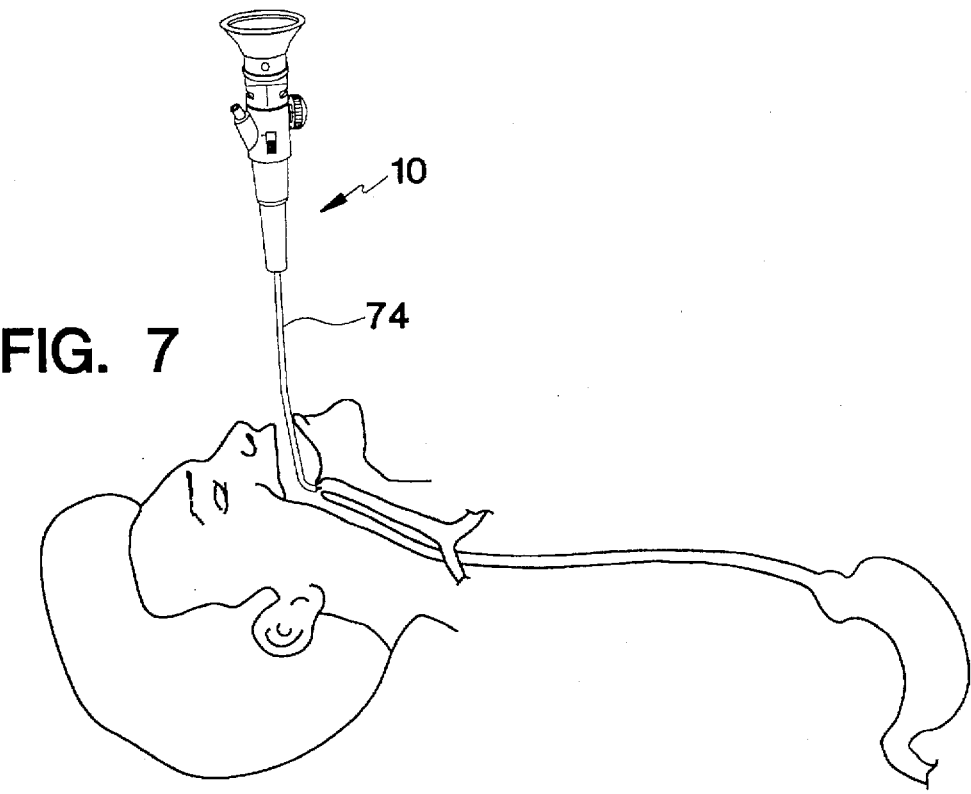
FIG. 7 is a side elevational view illustrating a first step in the operation of the intubator according to the present invention.
Figure 8:
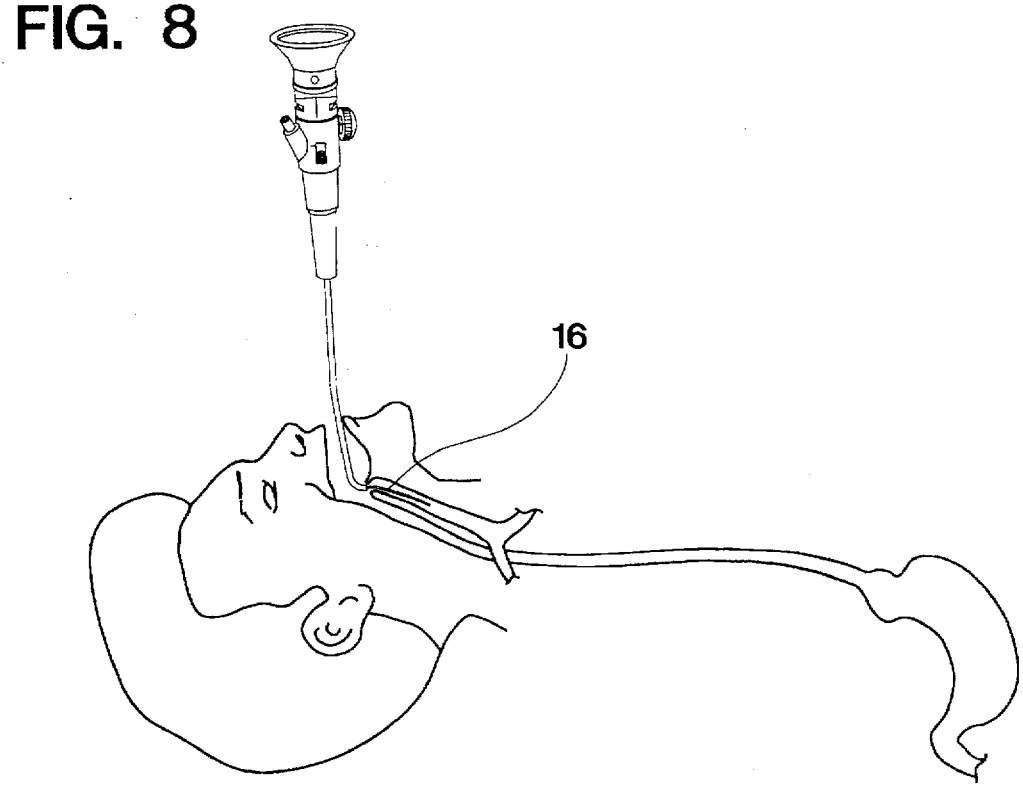
FIG. 8 is a side elevational view illustrating a second step in the operation of the intubator according to the present invention.

FIGS. 7 and 8 graphically illustrate the use of the intubator according to the present invention. Initially, as illustrated in FIG. 7, the intubator has an endotracheal tube attached thereon by a securing ring. The memory cylinder is positioned relative to the housing and the endotracheal tube is positioned on the memory cylinder such that the distal ends of the endotracheal tube, the memory cylinder and scope tube are flushed or aligned. The exterior of the memory cylinder can be lightly lubricated, if not provided with an antifriction coating such as Teflon. The outer surface of the endotracheal tube can also be lightly lubricated. The light is then illuminated by activating switch 60, or by attaching light cord 68 if using an external light source.

The distal end section of the intubator (i.e., the distal end of the memory cylinder) is manually or mechanically bent to a curve of between about 45 degrees to about 90 degrees.

The patient can be unconscious, anesthetized or have a topical anesthetic applied to the mouth and larynx to prevent reflex action. The operator stands at the head of the patient and holds the intubator by the handle. The distal end is then inserted into the patient's oral pharynx and hooked behind the back of the tongue. The handle is then placed in a straight upward position in the vertical plane. With slight manipulation, the orifice of the larynx can be localized quickly by the light reflex caused by the high intensity light at the distal end of the intubator illuminating the tissues through to the anterior neck. Specifically, the light passes through the thyroid membrane, the cricothyroid ligament, thyroid and cricoid cartilages, and the interior soft tissues and muscles of the patient's neck. When the light reflex is seen, the tip of the intubator is very close and most assuredly pointed at the larynx. In this manner, the larynx is easily located, without looking through the eye piece or at a monitor to find the larynx.

Secretions, abnormal anatomy, blood, fogging of the lens and difficulties focusing can lead to delays and loss of valuable time during emergency situations in finding the larynx for intubation. Flexible fiberoptic scopes are unyielding requiring considerable expertise and cannot be employed rapidly to find the larynx using the light reflex method. A light wand or lighted stylet, as used in the prior art, allows finding the larynx rapidly, but does not allow for the subsequent steps to guide the endotracheal tube into the larynx.

Once the light is seen, the operator looks into the optical viewing device (i.e., lens 38 or an external monitor) and can see the larynx. While holding the handle in either hand with the forefinger and thumb on the knob controlling the tip deflection of the scope tube, the other hand holds the outside of the endotracheal tube. The handle is then pushed and the control knob adjusted so that the intubator collapses advancing the scope tube out of the distal end of the memory cylinder and into the larynx and trachea. Once the distal end of the scope tube is in the proper position in the trachea, the intubator is locked into the compressed position by the frictional engagement, the bellows or the ratchet mechanism.

If secretions or blood obstruct vision, suctioning can be performed through coupling 40 and fluid conduit 22. Alternatively, a suction catheter can be inserted along the side of the intubator orally and aspirate the secretions. In non-emergent intubation, oxygen can be flushed through fluid conduit 22 or a topical anesthesia can be administered to the patient to attenuate reflexes in an awake and conscious patient.

With scope tube 16 in the trachea and locked into position, endotracheal tube 75 is pushed off securing ring 78 or other device securing the endotracheal tube on the memory cylinder, and is advanced into the trachea using the scope tube as a guiding stylet. The operator looks through the optical viewing device to visually confirm the placement of the endotracheal tube into the trachea. Once the endotracheal tube is in the trachea, the scope tube is withdrawn back into the memory cylinder by the relative axial movement of the housing relative to the memory cylinder. Once the memory cylinder and housing are in their original relative positions, the entire intubator is removed from the patient's oral pharynx, leaving the endotracheal tube within the patient's trachea.

Alternatively, once the endotracheal tube is properly placed within the trachea, the intubator can be removed from the patient without retracting the scope tube. However, this procedure is less preferred since it may subject the scope tube to damage.

By performing the intubation in this manner, the larynx orifice can be quickly localized and maintained with the semi-rigid, but malleable, memory cylinder, while allowing direct visualization of the larynx and insertion of the scope tube as a stylet. This intubation can be accomplished rapidly, particularly for emergency situations where time is of the essence. Additionally, the intubation can be easily preformed in non-emergent or routine circumstances which would otherwise be difficult. With a detachable connection between the memory cylinder and the housing, as provided by the housing tube or tubular connector, memory cylinders of different sizes can be easily and quickly secured to the housing to accommodate the particular characteristics of the patient. Additionally, the memory cylinder can be made to be disposable, while permitting reuse of the relatively expensive components of the handle and scope tube.

While various embodiments have been chosen to illustrate the invention, it will be understood by those skilled in the art that various changes and modifications can be made therein without departing from the scope of the invention as defined in the appended claims.

What is claimed is:

1. An intubation system, comprising:
    a housing having first and second axial ends;
    a memory cylinder mounted for axial movement within and relative to said housing, said memory cylinder extending from said second axial end of said housing and having a first axial end section received in said housing and a second axial end section spaced from said second axial end of said housing, said memory cylinder being bendable into different curved shapes and self-sustaining a curved shaped;

a scope tube coupled to and extending into said housing and slidably received in said memory cylinder, said scope tube including a light transmitting fiberoptic cable, a visual transmission fiberoptic cable and a fluid conduit, each of said cables and said conduits having a near end in said housing and a flexible distal end remote from said housing;

adjustment means for varying angular orientations of said distal ends of said cables and conduit relative to said near ends thereof;

light means in said housing for directing light into said light transmitting fiberoptic cable and emitting light from said distal end thereof;

lens means in said housing for viewing images adjacent said distal ends of said cables through said visual transmission fiberoptic cable; and coupling means, in said housing, for connecting fluid means to said near end of said fluid conduit for conveying fluids between said near and distal ends of said fluid conduit.

2. An intubation system according to claim 1 wherein said memory cylinder comprises securing means, fixed on an outer surface of said memory cylinder between said end sections of said memory cylinder, for attaching an endotracheal tube to and about said memory cylinder.

3. An intubation system according to claim 1 wherein an endotracheal tube is mounted coaxially on said memory cylinder.

4. An intubation system according to claim 1 wherein focusing means is coupled to said lens means for adjusting said lens means.

5. An intubation system according to claim 1 wherein said coupling means comprises a syringe port extending from said housing.

6. An intubation system according to claim 1 wherein said adjustment means comprises a rotatable knob mounted on said housing and an adjusting cable extending though said scope tube.

7. An intubation system according to claim 1 wherein said housing comprises a tubular connector extending axially at said second end of said housing, said memory cylinder being slidably received in said tubular connector.

8. An intubation system according to claim 7 wherein said tubular connector is a rigid tube fixed to said housing; and said memory cylinder frictionally and telescopically engages said tubular connector.

9. An intubation system according to claim 7 wherein said tubular connector comprises a compressible bellows.

10. An intubation system according to claim 9 wherein said bellows comprises securing means, on an end of said bellows remote from said housing, for attaching an endotracheal tube to said bellows and coaxially about said memory cylinder.

11. An intubation system according to claim 10 wherein said securing means comprises a tapered friction fitting.

12. An intubation system according to claim 7 wherein said tubular connector comprises ratchet means for connecting said memory cylinder to said tubular connector and for controlling relative axial movement therebetween.

13. An intubation system according to claim 12 wherein said ratchet means comprises a slot with steps in said tubular connector and a laterally projecting cog on said memory cylinder slidably received in said slot and releasably and selectively engageable with said steps.

14. An intubation system according to claim 1 wherein said housing comprises a jack for coupling an external light source to said housing.

15. An intubation system according to claim 1 wherein said housing comprises connection means for coupling said visual transmission fiberoptic cable to an external monitor.

16. An intubation system according to claim 1 wherein said memory cylinder is curved adjacent said second axial end section thereof.

17. An intubation system according to claim 1 wherein said memory cylinder is formed of semi-rigid metal.

18. An intubation system according to claim 1 wherein said memory cylinder is bendable without kinking to maintain an unchanged internal cross-sectional configuration after bending.

19. An intubation system according to claim 1 wherein said memory cylinder is mounted for axial movement within and relative to said housing without relative rotation of said housing and said memory cylinder.

20. An intubation system according to claim 1 wherein said second axial end of said memory cylinder has a blunt tip.

21. A method of intubating a patient, comprising the steps of:

mounting an endotracheal tube coaxially on an intubator having a housing, a memory cylinder and a scope tube axially slidable in the memory cylinder, with distal ends of the memory cylinder, endotracheal tube and scope tube being flush;

illuminating a light source and conducting light through a light fiberoptic cable in the scope tube;

bending a distal end of the memory cylinder into a curve of between about 45 degrees and about 90 degrees to form a self-sustaining curved distal end;

inserting the curved distal end of the memory cylinder into a patient's oral pharynx and behind the patient's tongue;

positioning the handle in a vertical plane;

manipulating the patient's larynx orifice by a light reflex emitted from the distal end of the scope tube and through the patient;

advancing the scope tube from the memory cylinder into the patient's larynx and trachea by collapsing the intubator at an axially adjustable connection between the housing and the memory cylinder, while viewing the larynx and trachea through a visual fiberoptic cable in the scope tube;

locking the axially adjustable connection between the housing and the memory cylinder;

pushing the endotracheal tube from the memory cylinder and into the patient's trachea using the scope tube as a guide, while visually confirming placement of the endotracheal tube in the trachea through the visual fiberoptic cable; and withdrawing the intubator from the patient, while leaving the endotracheal tube in the patient.

22. A method according to claim 21 wherein fluid is conveyed between the housing and the patient at the distal end of the scope tube through a fluid conduit in the scope tube.

23. A method according to claim 21 wherein the scope tube is withdrawn into the memory cylinder prior to removal of the intubator from the patient.

* * * * *